(12) United States Patent
Dohmen et al.

(10) Patent No.: US 10,104,486 B2
(45) Date of Patent: Oct. 16, 2018

(54) IN-EAR SENSOR CALIBRATION AND DETECTING SYSTEM AND METHOD

(71) Applicant: BRAGI GmbH, München (DE)

(72) Inventors: David K Dohmen, München (DE); Peter Vincent Boesen, München (DE)

(73) Assignee: BRAGI GmbH, München (DE)

( * ) Notice: Subject to any disclaimer, the term of this patent is extended or adjusted under 35 U.S.C. 154(b) by 0 days.

(21) Appl. No.: 15/414,327

(22) Filed: Jan. 24, 2017

(65) Prior Publication Data

US 2017/0215016 A1    Jul. 27, 2017

Related U.S. Application Data

(60) Provisional application No. 62/286,509, filed on Jan. 25, 2016.

(51) Int. Cl.
*H04R 29/00* (2006.01)
*H04R 1/10* (2006.01)

(52) U.S. Cl.
CPC ......... *H04R 29/001* (2013.01); *H04R 1/1091* (2013.01); *H04R 1/1016* (2013.01); *H04R 2420/07* (2013.01)

(58) Field of Classification Search
CPC .. H04R 1/1016; H04R 29/001; H04R 1/1091; H04R 2420/07; H04R 1/1025; H04R 2430/01; H04R 2460/03; H04R 5/033; H04R 5/04; A61B 5/121; A61B 5/7475; A61B 2560/0223; A61B 5/7225; A61B 2505/07; A61B 2560/0247; A61B 5/0022; A61B 5/0075; A61B 5/0816; A61B 5/082; A61B 5/0836; A61B 5/097; A61B 5/1032; A61B 5/4836; A61B 5/486

USPC ............. 381/56–58, 314, 312, 315, 23.1, 1
See application file for complete search history.

(56) References Cited

U.S. PATENT DOCUMENTS

| | | |
|---|---|---|
| 3,934,100 A | 1/1976 | Harada |
| 4,150,262 A | 4/1979 | Ono |
| 4,334,315 A | 6/1982 | Ono et al. |
| 4,375,016 A | 2/1983 | Harada |
| 4,588,867 A | 5/1986 | Konomi |
| 4,654,883 A | 3/1987 | Iwata |
| 4,682,180 A | 7/1987 | Gans |

(Continued)

FOREIGN PATENT DOCUMENTS

| | | |
|---|---|---|
| EP | 1017252 A2 | 7/2000 |
| EP | 2903186 A1 | 8/2015 |

(Continued)

OTHER PUBLICATIONS

Announcing the $3,333,333 Stretch Goal (Feb. 24, 2014).

(Continued)

*Primary Examiner* — Lun-See Lao
(74) *Attorney, Agent, or Firm* — Goodhue, Coleman & Owens, P.C.

(57) ABSTRACT

A system, method and one or more wireless earpieces for calibrating one or more wireless earpieces. An indication that the calibration of the one or more wireless earpieces is required is received. Sensors of the one or more wireless earpieces are calibrated in response to receiving the indication. Calibration information is analyzed. A determination is made whether the calibration is successful utilizing the calibration information.

10 Claims, 4 Drawing Sheets

(56) References Cited

U.S. PATENT DOCUMENTS

| | | | |
|---|---|---|---|
| 4,791,673 A | 12/1988 | Schreiber | |
| 4,865,044 A | 9/1989 | Wallace et al. | |
| 5,191,602 A | 3/1993 | Regen et al. | |
| 5,201,007 A | 4/1993 | Ward et al. | |
| 5,280,524 A | 1/1994 | Norris | |
| 5,295,193 A | 3/1994 | Ono | |
| 5,298,692 A | 3/1994 | Ikeda et al. | |
| 5,343,532 A | 8/1994 | Shugart | |
| 5,363,444 A | 11/1994 | Norris | |
| 5,497,339 A | 3/1996 | Bernard | |
| 5,606,621 A | 2/1997 | Reiter et al. | |
| 5,613,222 A | 3/1997 | Guenther | |
| 5,692,059 A | 11/1997 | Kruger | |
| 5,721,783 A | 2/1998 | Anderson | |
| 5,749,072 A | 5/1998 | Mazurkiewicz et al. | |
| 5,771,438 A | 6/1998 | Palermo et al. | |
| 5,802,167 A | 9/1998 | Hong | |
| 5,929,774 A | 7/1999 | Charlton | |
| 5,933,506 A | 8/1999 | Aoki et al. | |
| 5,949,896 A | 9/1999 | Nageno et al. | |
| 5,987,146 A | 11/1999 | Pluvinage et al. | |
| 6,021,207 A | 2/2000 | Puthuff et al. | |
| 6,054,989 A | 4/2000 | Robertson et al. | |
| 6,081,724 A | 6/2000 | Wilson | |
| 6,094,492 A | 7/2000 | Boesen | |
| 6,111,569 A | 8/2000 | Brusky et al. | |
| 6,112,103 A | 8/2000 | Puthuff | |
| 6,157,727 A | 12/2000 | Rueda | |
| 6,167,039 A | 12/2000 | Karlsson et al. | |
| 6,181,801 B1 | 1/2001 | Puthuff et al. | |
| 6,208,372 B1 | 3/2001 | Barraclough | |
| 6,275,789 B1 | 8/2001 | Moser et al. | |
| 6,339,754 B1 | 1/2002 | Flanagan et al. | |
| 6,408,081 B1 | 6/2002 | Boesen | |
| D464,039 S | 10/2002 | Boesen | |
| 6,470,893 B1 | 10/2002 | Boesen | |
| D468,299 S | 1/2003 | Boesen | |
| D468,300 S | 1/2003 | Boesen | |
| 6,542,721 B2 | 4/2003 | Boesen | |
| 6,560,468 B1 | 5/2003 | Boesen | |
| 6,654,721 B2 | 11/2003 | Handelman | |
| 6,664,713 B2 | 12/2003 | Boesen | |
| 6,694,180 B1 | 2/2004 | Boesen | |
| 6,718,043 B1 | 4/2004 | Boesen | |
| 6,738,485 B1 | 5/2004 | Boesen | |
| 6,748,095 B1 | 6/2004 | Goss | |
| 6,754,358 B1 | 6/2004 | Boesen et al. | |
| 6,784,873 B1 | 8/2004 | Boesen et al. | |
| 6,823,195 B1 | 11/2004 | Boesen | |
| 6,852,084 B1 | 2/2005 | Boesen | |
| 6,879,698 B2 | 4/2005 | Boesen | |
| 6,892,082 B2 | 5/2005 | Boesen | |
| 6,920,229 B2 | 7/2005 | Boesen | |
| 6,952,483 B2 | 10/2005 | Boesen et al. | |
| 6,987,986 B2 | 1/2006 | Boesen | |
| 7,136,282 B1 | 11/2006 | Rebeske | |
| 7,203,331 B2 | 4/2007 | Boesen | |
| 7,209,569 B2 | 4/2007 | Boesen | |
| 7,215,790 B2 | 5/2007 | Boesen et al. | |
| 7,463,902 B2 | 12/2008 | Boesen | |
| 7,508,411 B2 | 3/2009 | Boesen | |
| 7,983,628 B2 | 7/2011 | Boesen | |
| 8,140,357 B1 | 3/2012 | Boesen | |
| 2001/0005197 A1 | 6/2001 | Mishra et al. | |
| 2001/0027121 A1 | 10/2001 | Boesen | |
| 2001/0056350 A1 | 12/2001 | Calderone et al. | |
| 2002/0002413 A1 | 1/2002 | Tokue | |
| 2002/0007510 A1 | 1/2002 | Mann | |
| 2002/0010590 A1 | 1/2002 | Lee | |
| 2002/0030637 A1 | 3/2002 | Mann | |
| 2002/0046035 A1 | 4/2002 | Kitahara et al. | |
| 2002/0057810 A1 | 5/2002 | Boesen | |
| 2002/0076073 A1 | 6/2002 | Taenzer et al. | |
| 2002/0118852 A1 | 8/2002 | Boesen | |
| 2003/0065504 A1 | 4/2003 | Kraemer et al. | |
| 2003/0100331 A1 | 5/2003 | Dress et al. | |
| 2003/0104806 A1 | 6/2003 | Ruef et al. | |
| 2003/0115068 A1 | 6/2003 | Boesen | |
| 2003/0125096 A1 | 7/2003 | Boesen | |
| 2003/0218064 A1 | 11/2003 | Conner et al. | |
| 2004/0070564 A1 | 4/2004 | Dawson et al. | |
| 2004/0160511 A1 | 8/2004 | Boesen | |
| 2005/0043056 A1 | 2/2005 | Boesen | |
| 2005/0125320 A1 | 6/2005 | Boesen | |
| 2005/0148883 A1 | 7/2005 | Boesen | |
| 2005/0165663 A1 | 7/2005 | Razumov | |
| 2005/0196009 A1 | 9/2005 | Boesen | |
| 2005/0251455 A1 | 11/2005 | Boesen | |
| 2005/0266876 A1 | 12/2005 | Boesen | |
| 2006/0029246 A1 | 2/2006 | Boesen | |
| 2006/0074671 A1 | 4/2006 | Farmaner et al. | |
| 2006/0074808 A1 | 4/2006 | Boesen | |
| 2008/0254780 A1 | 10/2008 | Kuhl et al. | |
| 2009/0017881 A1 | 1/2009 | Madrigal | |
| 2010/0172523 A1* | 7/2010 | Burns | H04R 25/50 381/312 |
| 2010/0320961 A1 | 12/2010 | Castillo et al. | |
| 2011/0286615 A1 | 11/2011 | Olodort et al. | |
| 2012/0148054 A1* | 6/2012 | Rank | H04R 25/552 381/23.1 |
| 2013/0083933 A1* | 4/2013 | Aase | H04R 1/1041 381/58 |
| 2013/0149969 A1* | 6/2013 | Smailagic | H04M 1/24 455/41.2 |
| 2014/0122116 A1 | 5/2014 | Smythe | |
| 2014/0222462 A1 | 8/2014 | Shakil et al. | |
| 2014/0270227 A1 | 9/2014 | Swanson | |
| 2015/0023534 A1* | 1/2015 | Shennib | H04R 25/70 381/314 |

FOREIGN PATENT DOCUMENTS

| | | |
|---|---|---|
| GB | 2074817 | 4/1981 |
| JP | 06292195 | 10/1998 |
| WO | 2014043179 A2 | 3/2014 |
| WO | 2015110577 A1 | 7/2015 |
| WO | 2015110587 A1 | 7/2015 |

OTHER PUBLICATIONS

Bhidayasiri, "Differential diagnosis of common tremor syndromes", Postgrad Med J vol. 81 pp. 756-762 (2005).

BRAGI Is on Facebook (2014).

BRAGI Update—Arrival of Prototype Chassis Parts—More People—Awesomeness (May 13, 2014).

BRAGI Update—Chinese New Year, Design Verification, Charging Case, More People, Timeline(Mar. 6, 2015).

BRAGI Update—First Sleeves From Prototype Tool—Software Development Kit (Jun. 5, 2014).

BRAGI Update—Let's Get Ready to Rumble, A Lot to Be Done Over Christmas (Dec. 22, 2014).

BRAGI Update—Memories From April—Update on Progress (Sep. 16, 2014).

BRAGI Update—Memories from May—Update on Progress—Sweet (Oct. 13, 2014).

BRAGI Update—Memories From One Month Before Kickstarter—Update on Progress (Jul. 10, 2014).

BRAGI Update—Memories From the First Month of Kickstarter—Update on Progress (Aug. 1, 2014).

BRAGI Update—Memories From the Second Month of Kickstarter—Update on Progress (Aug. 22, 2014).

BRAGI Update—New People @BRAGI—Prototypes (Jun. 26, 2014).

BRAGI Update—Office Tour, Tour to China, Tour to CES (Dec. 11, 2014).

BRAGI Update—Status on Wireless, Bits and Pieces, Testing—Oh Yeah, Timeline(Apr. 24, 2015).

BRAGI Update—The App Preview, The Charger, The SDK, BRAGI Funding and Chinese New Year (Feb. 11, 2015).

(56) References Cited

OTHER PUBLICATIONS

BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back to China, Backer Day, on Track(May 16, 2015).
BRAGI Update—Beta2 Production and Factory Line(Aug. 20, 2015).
BRAGI Update—Certifications, Production, Ramping Up.
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2014).
BRAGI Update—On Track, Design Verification, How It Works and What's Next(Jul. 15, 2015).
BRAGI Update—On Track, on Track and Gems Overview.
BRAGI Update—Status on Wireless, Supply, Timeline and Open House@BRAGI(Apr. 1, 2015).
BRAGI Update—Unpacking Video, Reviews on Audio Perform and Boy Are We Getting Close(Sep. 10, 2015).
Healthcare Risk Management Review, "Nuance updates computer-assisted physician documentation solution" (Oct. 20, 2016).
Hoyt et. al., "Lessons Learned from Implementation of Voice Recognition for Documentation in the Military Electronic Health Record System", The American Health Information Management Association (2017).
Last Push Before the Kickstarter Campaign Ends on Monday 4pm CET (Mar. 28, 2014).
Li et. al, "Stress and Emotion Classification Using Jitter and Shimmer Features", ICASSP (2007) pp. 1081-1084.
Staab, Wayne J., et al., "A One-Size Disposable Hearing Aid is Introduced", The Hearing Journal 53(4):36-41) Apr. 2000.
Stretchgoal—It's Your Dash (Feb. 14, 2014).
Stretchgoal—The Carrying Case for the Dash (Feb. 12, 2014).
Stretchgoal—Windows Phone Support (Feb. 17, 2014).
The Dash + The Charging Case & The BRAGI News (Feb. 21, 2014).
The Dash—A Word From Our Software, Mechanical and Acoustics Team + An Update (Mar. 11, 2014).
Update From BRAGI—$3,000,000—Yipee (Mar. 22, 2014).

* cited by examiner

IN-EAR SENSOR CALIBRATION AND DETECTING SYSTEM AND METHOD

PRIORITY STATEMENT

This application claims priority to U.S. Provisional Patent Application 62/286,509, filed on Jan. 25, 2016, and entitled In Ear Sensor Calibration and Detection System and Method, hereby incorporated by reference in its entirety.

BACKGROUND

I. Field of the Disclosure

The illustrative embodiments relate to wireless earpieces. More specifically, but not exclusively, the illustrative embodiments relate to calibrating sensors of the wireless earpieces for improved performance.

II. Description of the Art

The growth of wearable devices is increasing significantly. This growth is fostered by the decreasing size of transceivers, chips, and other components as well as enhanced transaction standards and protocols. Ensuring the wearables perform accurate measurements may be difficult because of different positioning on the user, differences in anatomically configuration of each user, and use environments.

SUMMARY OF THE DISCLOSURE

One embodiment provides a system, method and one or more wireless earpieces for calibrating one or more wireless earpieces. An indication that the calibration of the one or more wireless earpieces is required is received. Sensors of the one or more wireless earpieces are calibrated in response to receiving the indication. Calibration information is analyzed. A determination is made whether the calibration is successful utilizing the calibration information. Another embodiment provides a wireless earpiece including a processor and a memory storing a set of instructions. The set of instructions are executed to perform the method described.

Another embodiment provides a wireless earpiece. The wireless earpiece includes a frame for fitting in an ear of a user. The wireless earpiece further includes a logic engine controlling functionality of the wireless earpiece. The wireless earpiece further includes a number of sensors reading biometric identifiers of a user. The logic engine identifies the user utilizing the biometric identifiers, calibrates sensors of the one or more wireless earpieces based on the user and in response to receiving the indication, analyzes calibration information, and determines whether the calibration is successful utilizing the calibration information.

BRIEF DESCRIPTION OF THE DRAWINGS

Illustrated embodiments of the present invention are described in detail below with reference to the attached drawing figures, which are incorporated by reference herein, and where.

DETAILED DESCRIPTION OF THE DISCLOSURE

Figure 1:
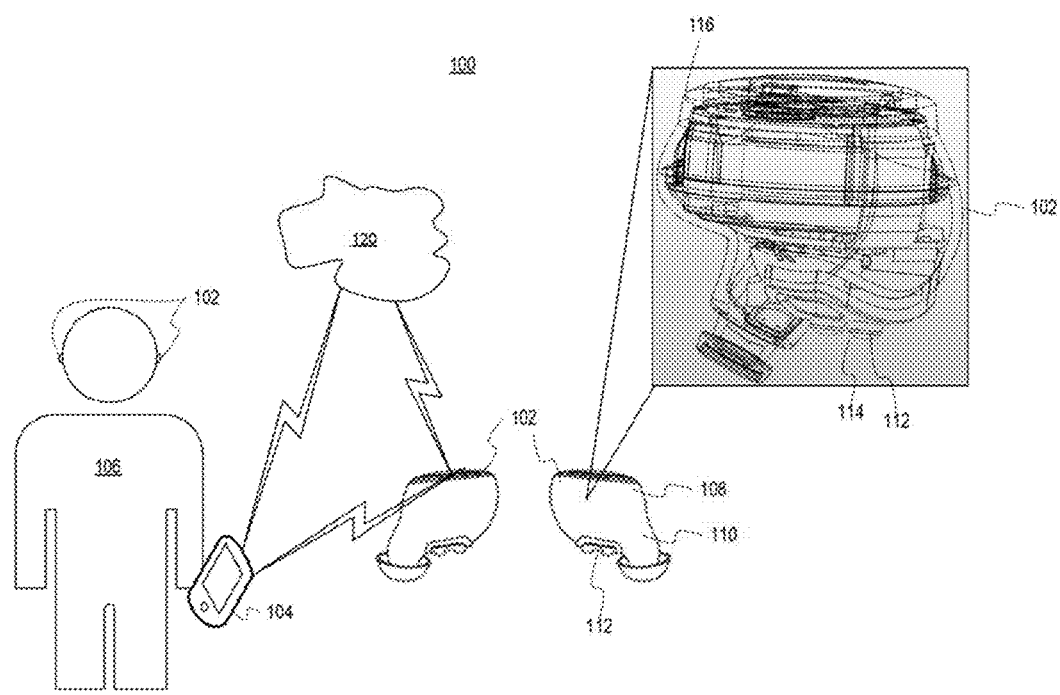
FIG. 1 is a pictorial representation of a communication environment in accordance with an illustrative embodiment.

The illustrative embodiments provide a system, method, and apparatus for calibrating wireless earpieces to perform more accurate measurements. Calibration may refer to any of an initial calibration or any number of re-calibrations that may be required during the life cycle of the wireless earpieces. In one embodiment, one or more sensor arrays of the wireless earpieces may be calibrated for a user. Different calibration settings, preferences, and schemes may be determined for different users that may utilize a wireless earpiece. Given the unique topography of each user's ears, the actual position of the wireless earpieces varies not only person to person, but from ear-to-ear as well requiring accurate calibration of the sensors. Calibration of the sensors is performed to deliver consistent and reliable information and data to the user regarding the user (e.g., biometrics, position, orientation, etc.), the environment, as well as performance of the wireless earpieces.

In one embodiment, the wireless earpieces may request the user position the wireless earpieces in a correct position before a calibration process begins. For example, the wireless earpieces may have default or correct positioning information that may be utilized for comparison purposes. Once the wireless earpieces are properly positioned, the user may be directed to perform various head, neck, and/or body motions and gestures to calibrate the sensors of the wireless earpieces. The motions of the user may be associated with various responses, cone ands, actions, or activities of the user for providing more accurate information. For example, one or more processors of the wireless earpieces may execute an algorithm to process the incoming sensor measurements that are associated with the user action (e.g., motion, position, orientation, etc.). The calibration process leads to improved recognition rates for patterns, gestures, activities, and actions. The wireless earpieces may also record or log noise associated with the wireless earpieces to generate a noise floor that is utilized to more accurately make sensor measurements as well as process those measurements. The sensors of the wireless earpieces may include accelerometers, gyroscopes, microphones, camera or imaging devices, contact/conductivity sensors, pulse oximeters, and so forth.

In one embodiment, the wireless pieces may generate a topographical map of the users inner and/or outer ear and head area to both identify the user and ensure proper positioning. As a result, any number of alerts or prompts may be played to the user indicating that one or more of the wireless earpieces are improperly positioned in response to detecting a change or variation from the norm. For example, an audio alert indicating "the left earpiece is improperly positioned" may be played to the user in response to detecting an aberration from the expected norm any time or during the calibration process of the wireless earpieces. The standard settings, norms, baseline, and default position as well as variations, aberrations, and so forth may be saved within the wireless earpieces or one or more connected wireless devices (e.g., cell phones, tablets, smart cards, smart wearables, personal computers, vehicles, home automation devices, appliances, radio frequency identification tags, etc.). In addition to saving the data points in the onboard memory systems of the wireless earpieces, the data may be saved to an application running on a wirelessly linked device.

The calibration process may rapidly detect significant errors in earpiece placement (e.g., one or both of the devices being placed into the respective ears upside down). The sensor measurements may be quickly read to provide the user audio, text, tactile, or other feedback to adjust the wireless earpieces. In addition, if the wireless earpieces detect excessive noise, such as tremors, slippage of the earpieces, or audio or electronic noise, the user may be prompted to take one or more actions correcting the situation.

The wireless earpieces are worn in the ear of the user. For example, the wireless earpieces are configured to fit at least partially into an external auditory canal of the user. The ear canal is a rich space for obtaining biometric measurements about the user as well as stabilizing the wireless earpieces as they are worn. The wireless earpieces may be utilized during a number of rigorous physical activities that require stability. The shape and configuration of the wireless earpieces allow the wireless earpieces to be worn for long periods of time while gathering valuable information utilizing the sensors of the wireless earpieces. Important measurements taken by the sensors may include pulse rate, blood oxygenation, microphone, position/orientation, location, temperature, altitude, cadence, calorie expenditure, and so forth.

The wireless earpieces may include any number of sensor arrays configured to capture information about the user. The large amount of data may be utilized to provide valuable information to the user and thus thorough calibration of the sensors is important. The wireless earpieces may learn over time in response to calibration processes performed and historical information. Alerts may be played to the user indicating the status of the calibration process (e.g., initiated, in process, pending, awaiting verification, approved, rejected, etc.).

FIG. 1 is a pictorial representation of a communication environment 100 in accordance with an illustrative embodiment. The wireless earpieces 102 may be configured to communicate with each other and with one or more wireless devices, such as a wireless device 104. The wireless earpieces 102 may be worn by a user 106 and are shown as worn and separately from their positioning within the ears of the user 106 for purposes of visualization. A block diagram of the wireless earpieces 102 if further shown in FIG. 2 to further illustrate components and operation of the wireless earpieces 102.

In one embodiment, the wireless earpieces 102 includes a frame 108 shaped to fit substantially within the ears of the user 106. The frame 108 is a support structure that at least partially encloses and houses the electronic components of the wireless earpieces 102. The frame 108 may be composed of a single structure or multiple structures that are interconnected. The frame 108 defines an extension 110 configured to fit substantially within the ear of the user 106. The extension 110 may house one or more speakers or vibration components for interacting with the user. The extension 110 may be removably covered by one or more sleeves. The sleeves may be changed to fit the size and shape of the user's ears. The sleeves may come in various sizes and may have extremely tight tolerances to fit the user 106 and one or more other users that may utilize the wireless earpieces 102 during their expected lifecycle. In another embodiment, the sleeves may be custom built to support the interference fit utilized by the wireless earpieces 102 while also being comfortable while worn.

In one embodiment, the frame 108 or the extension 110 (or other portions of the wireless earpieces 102) may include sensors 112 for sensing pulse, blood oxygenation, temperature, voice characteristics, skin conduction, glucose levels, impacts, activity level, position, location, orientation, as well as any number of internal or external user biometrics. In other embodiments, the sensors 112 may be internally positioned within the wireless earpieces 102. For example, the sensors 112 may represent metallic contacts, optical interfaces, or micro-delivery systems for receiving and delivering information. Small electrical charges may be sensed as well as passed through the sensors 112 to analyze the biometrics of the user 106 including pulse, skin conductivity, blood analysis, sweat levels, band so forth. Sensors 112 may also be utilized to provide a small electrical current which may be useful for alerting the user, stimulating blood flow, alleviating nausea, or so forth.

In some applications, temporary adhesives or securing mechanisms (e.g., clamps, straps, lanyards, extenders, etc.) may be utilized to ensure that the wireless earpieces 102 remain in the ears of the user 106 even during the most rigorous and physical activities. For example, the wireless earpieces 102 may be utilized during marathons, swimming, team sports, biking, hiking, parachuting, or so forth. The wireless earpieces 102 may be configured to play music or audio, receive and make phone calls or other communications, determine ambient environmental conditions (e.g., temperature, altitude, location, speed, heading, etc.), read user biometrics (e.g., heart rate, motion, temperature, sleep, blood oxygenation, voice output, calories burned, forces experienced, etc.), and receive user input, feedback, or instructions. The wireless device 104 or the wireless earpieces 102 may communicate directly or indirectly with one or more wired or wireless networks, such as a network 120. The wireless earpieces 102 may utilize a self-calibration process to automatically calibrate sensors 112 of the wireless earpieces for more accurate readings.

The wireless earpieces 102 may determine their position with respect to each other as well as the wireless device 104. For example, position information for the wireless earpieces 102 and the wireless device 104 may determine proximity of the devices in the communication environment 100. For example, global positioning information, wireless triangulation, or signal strength/activity may be utilized to determine proximity and distance of the devices to each other in the communication environment 100. In one embodiment, the distance information may be utilized to determine whether the wireless 1.0 earpieces 102 are both being worn (e.g., should be experiencing similar environmental conditions, noise, etc.).

In one embodiment, the wireless earpieces 102 and the corresponding sensors 112 (whether internal or external) may be configured to take a number of measurements or log information during normal usage. The sensor measurements may be utilized to extrapolate other measurements, factors, or conditions applicable to the user 106. For example, the sensors 112 may monitor the user's heartbeat or EKG to determine the user's unique pattern or characteristics. The user 106 or another party may configure the wireless earpieces 102 directly or through a connected device and app (e.g., mobile app with a graphical user interface) to store or share information, audio, images, and other data. Some examples of standard usage may include detecting and recording a heartbeat, setting a biometric for transaction authentication, setting a gesture/input for performing an action (e.g., playing music, opening an application, providing an audio indication of biometric feedback, etc.), active participation in a conversation, listening to music, or so forth.

The wireless earpieces 102 may calibrate the sensors 112 during an initial set up process, during start up, based on a failure, or in response to a user request. In one embodiment, each of the sensors 112 of the wireless earpieces 102 may perform baseline readings to determine whether the wireless earpieces 102 are properly positioned and whether accurate sensor measurements are being made. For example, the wireless earpieces 102 may scan the topography of the user's ear and head. The scan is compared against a baseline scan when the wireless earpieces 102 were properly positioned to determine whether the wireless earpieces are accurately positioned. Instructions may be provided to the user to adjust the position of the wireless earpieces 102 as necessary to reach a desired or proper position. For example, the wireless earpieces 102 may instruct the user to "turn the left earpiece counterclockwise about 2 millimeters."

In another embodiment, the user 106 may not be required to reposition the wireless earpieces 102. Instead, the wireless earpieces 102 may adapt the sensors 112 to their respective positions within the ears of the user 106. The wireless earpieces 102 may perform calibration processes and tests to calibrate the wireless earpieces 102 based on the current positioning within the ears of the user. The wireless earpieces 102 may also prompt the user to take a number of actions, such as "say your name followed by the phrase 'I am testing the accuracy and sensors of The Dash for maximum performance. 1, 2, 3, 4, 5, 6, 7, 8, 9, 10, this is only a test.'" The wireless earpieces 102 may also pose questions to determine information, such as what position are you in, what activity are you engaged in, where are you (e.g., outside, park, home, etc.), or any number of other questions that may be utilized Any number of sensor calibration processes may be performed including removing structural errors in the sensor outputs. Structural errors are differences between the sensors 112 expected output and the measured output which are ascertainable every time a new sensor measurement is taken. In one embodiment, the sensor readings from the left wireless earpiece may also be utilized to calibrate the sensor readings of the right wireless earpiece. In another embodiment, sensor measurements taken by the wireless device 104 may be utilized to calibrate the sensors 112 of the wireless earpieces (e.g., outside temperature, audio noise level, etc.). Likewise, sensor measurements from externally connected devices may also be utilized. Calibration of the sensors 112 is also important because of natural and manufacturing variations between sensors. For example, even two temperature sensors from the same manufacturer production run may yield slightly different readings. The sensors 112 may also require calibration and recalibration based on heat, cold, light conditions, altitude, pressure, alignment of the devices, shock, noise, hysteresis, variation of components (e.g., analog-to-digital converters), humidity, radiation, and other factors. The sensors 112 may utilize any number of zeroing, biasing, automatic adjustments, or manual adjustment techniques for calibration purposes. The user 106 may interact with the wireless earpieces 102 directly or through a user interface of the wireless device 104.

The user 106 or another party may also utilize the wireless device 104 to associate biometric information and conditions with the actual or perceived status of the user 106. As a result, the wireless earpieces 102 may be adjusted or trained over time to become even more accurate in reading biometric information of the user 106 for purposes of calibration. The wireless earpieces 102 may utilize historical information to generate default values, baselines, thresholds, policies, or settings for determining when and how the sensors are calibrated utilizing information and data, such as the user's biometric identifiers.

The wireless earpieces 102 may include any number of sensors 112 and logic for measuring and determining user biometrics, such as pulse rate, skin conduction, blood oxygenation, temperature, calories expended, voice and audio output, position, and orientation (e.g., body, head, etc.). The sensors 112 may also determine the user's location, position, velocity, impact levels, and so forth. The sensors 112 may also receive user input and convert the user input into commands or selections made across the personal devices of the personal area network. For example, the user input detected by the wireless earpieces 102 may include voice commands, head motions, finger taps, finger swipes, motions or gestures, or other user inputs sensed by the wireless earpieces. The user input may be measured by the wireless earpieces 102 and converted into internal commands or external commands that may be sent to one or more external devices, such as the wireless device 104, a tablet computer, or so forth. For example, the user 106 may create a specific head motion and voice command that when detected by the wireless earpieces 102 are utilized to authenticate a transaction or secure communication to or from the wireless earpieces 102.

The sensors 112 may make all of the measurements with regard to the user 106 or may communicate with any number of other sensory devices in the communication environment 100 to measure information and data about the user 106 as well as the communication environment 100 itself. In one embodiment, the communication environment 100 may represent all or a portion of a personal area network. The wireless earpieces 102 may be utilized to control, communicate, manage, or interact with a number of other wearable devices or electronics, such as smart glasses, helmets, smart glass, watches or wrist bands, other wireless earpieces, chest straps, implants, displays, clothing, or so forth. A personal area network is a network for data transmissions among devices, such as personal computing, communications, camera, vehicles, entertainment, an medical devices. The personal area network may utilize any number of wired, wireless, or hybrid configurations and may be stationary or dynamic. For example, the personal area network may utilize wireless network protocols or standards, such as INSTEON, IrDA, Wireless USB, Bluetooth, Z-Wave, ZigBee, Wi-Fi, ANT+ or other applicable radio frequency signals. In one embodiment, the personal area network may move with the user 106.

In other embodiments, the communication 100 may include any number of devices, components, or so forth that may communicate with each other directly or indirectly through a wireless (or wired) connection, signal, or link. The communication environment 100 may include one or more networks and network components and devices represented by the network 120, such as routers, servers, signal extenders, intelligent network devices, computing devices, or so forth. In one embodiment, the network 120 of the communication environment 100 represents a personal area network as previously disclosed. The network 120 may also represent a number of different network types and service providers.

Communications within the communication environment 100 may occur through the network 120 or may occur directly between devices, such as wireless earpieces 102 and the wireless device 104, or indirectly through a network, such as a Wi-Fi network. The network 120 may communicate with or include a wireless network, such as a Wi-Fi, cellular (e.g., 3G, 4G, 5G, PCS, GSM, etc.), Bluetooth, or other short range or long range radio frequency network. The network 120 may also include or communicate with any number of hard wired networks, such as local area networks, coaxial networks, fiber-optic networks, network adapters, or so forth. Communications within the communication environment 100 may be operated by one or more users, service providers (e.g., secure, public, private, etc.), or network providers.

The wireless earpieces 102 may play, communicate, or utilize any number of alerts or communications to indicate that the status of the calibration process. For example, one or more alerts may indicate when calibration is pending, in process, requires user interaction, and/or completed with specific tones, verbal acknowledgements, tactile feedback, or other forms of communicated messages. For example, an alert may be played during each stage of the calibration process. The corresponding alert may also be communicated to the user 106, and the wireless device 104.

In other embodiments, the wireless earpieces 102 may also vibrate, flash, play a tone or other sound, or give other indications of the calibration process status in order to prompt user actions (e.g., providing a biometric reading, perform a gesture, specifically position the user's head, etc.) or implement any number of associated steps. The wireless earpieces 102 may also communicate an alert to the wireless device 104 that shows up as a notification, message, or other indicator indicating the necessity for calibration/re-calibration or a changed status of the calibration process.

The wireless earpieces 102 as well as the wireless device 104 may include logic for automatically implementing calibration in response to set-up, start-up, condition changes, event happenings, user requests or various other conditions and factors of the communication environment 100. For example, the wireless device 104 may communicate instructions received from the wireless earpieces 102 for the user 106 to push the wireless earpieces 102 back to a proper position in the user's ears. The wireless device 104 may include an application that displays instructions and information to the user 106 in response to calibration being needed or required.

In one embodiment, the wireless device 104 may utilize short-range or long-range wireless communications to communicate with the wireless earpieces 102 through a wireless signal or devices of the communication environment 100. For example, the wireless device 104 may include a Bluetooth and cellular transceiver within the embedded logical components. For example, the wireless signal may be a Bluetooth, Wi-Fi, Zigbee, Ant+, near-field magnetic induction (NFMI), or other short range wireless communication.

The wireless device 104 may represent any number of wireless or wired electronic communications or computing devices, such as smart phones, laptops, desktop computers, control systems, tablets, displays, gaming devices, music players, personal digital assistants, vehicle systems, or so forth. The wireless device 104 may communicate utilizing any number of wireless connections, standards, or protocols (e.g., near field communications, NFMI, Bluetooth, Wi-Fi, wireless Ethernet, etc,). For example, the wireless device 104 may be a touch screen cellular phone that communicates with the wireless earpieces 102 utilizing Bluetooth communications. The wireless device 104 may implement and utilize any number of operating systems, kernels, instructions, or applications that may make use of the available sensor data sent from the wireless earpieces 102. For example, the wireless device 104 may represent any number of android, iOS, Windows, open platforms, or other systems and devices. Similarly, the wireless device 104 or the wireless earpieces 102 may execute any number of applications that utilize the user input, proximity data, biometric data, and other feedback from the wireless earpieces 102 to initiate, authorize, or perform calibration and the associated tasks.

As noted, the layout of the internal components of wireless earpieces 102 and the limited space available for a product of limited size may affect where the sensors 112 may be positioned. The positions of the sensors 112 within each of the wireless earpieces 102 may vary based on the model, version, and iteration of the wireless earpiece design and manufacturing process.

Figure 2:
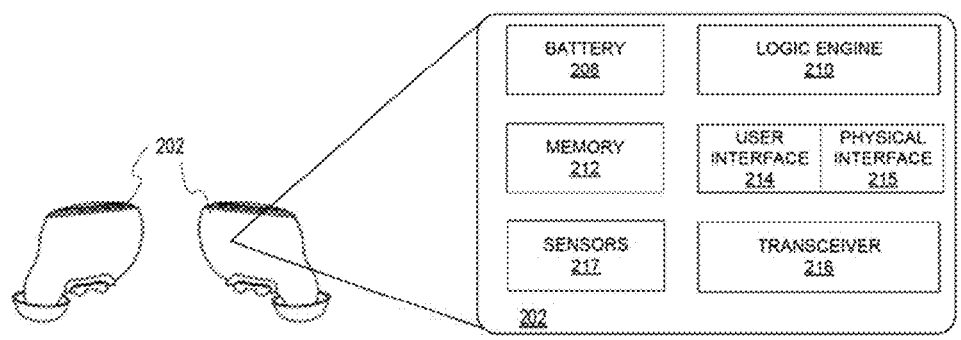
FIG. 2 is a block diagram of wireless earpieces in accordance with an illustrative embodiment.

FIG. 2 further illustrates a block diagram of the wireless earpieces 202. As noted, the components of the wireless earpieces 202 may be described collectively rather than individually. The wireless earpieces 202 may be wirelessly linked to any number of wireless devices (not shown), such as the wireless device 104 of FIG. 1. For example, wireless devices may include wearable devices, communications devices, computers, entertainment devices, vehicle systems, exercise equipment, construction or troubleshooting equipment, or so forth. Sensor measurements, user input, and commands may be received from either the wireless earpieces 202 or the wireless device for processing and implementation on either of the devices (or other externally connected devices). Reference to the wireless earpieces 202 may descriptively or functionally refer to either the pair of wireless earpieces (wireless earpieces) or individual wireless earpieces (left wireless earpiece and right wireless earpiece) without limitation.

In some embodiments, the wireless device may also act as a logging tool for sensor data or measurements made by the wireless earpieces 202. For example, the wireless device may receive and share data captured by the wireless earpieces 202 in real-time including biometric information, such as a status of the user (e.g., physical, emotional, etc.). As a result, the wireless device may be utilized to store, display, and synchronize sensor data received from the wireless earpieces 202. For example, the wireless device may display user pulse rate, temperature, proximity, location, blood oxygenation, distance, calories burned, and so forth as measured by the wireless earpieces 202. The wireless device may also store information regarding known or typical conditions (e.g., noise levels, environmental conditions, etc.) for specific locations that may be utilized to perform sensor calibration or biasing. The wireless device may be configured to receive and display alerts that indicate when calibration has been initiated, processed, and completed.

In one embodiment, the wireless earpieces 202 may include a battery 208, a logic engine 210, a memory 212, a user interface 214, a physical interface 215, a transceiver 216, and sensors 217. The wireless earpieces 202 and the wireless device may have any number of electrical configurations, shapes, and colors and may include various circuitry, connections, and other components utilized to perform the illustrative embodiments.

The battery 208 is a power storage device configured to power the wireless earpieces 202. In other embodiments, the battery 208 may represent a fuel cell, thermal electric generator, piezo electric charger, solar charger, ultra-capacitor, or other existing or developing power storage technologies. The sensors 217 may also be utilized to measure the temperature of the battery 208 and the condition of internal components of the wireless earpieces 202. The sensors 217 may also be utilized to determine data about external conditions and factors applicable to the user, the user's environment, a communicating wireless device, or so forth. Other conditions and factors sensed by the sensors 217 (e.g., water/humidity, pressure, blood oxygenation, blood content levels, altitude, position, impact, radiation, etc.) may also be determined with the data being processed by the logic engine 210.

The logic engine 210 is the logic that controls the operation and functionality of the wireless earpieces 202. The logic engine 210 may include circuitry, chips, and other digital logic. The logic engine 210 may also include programs, scripts, and instructions that may be implemented to operate the logic engine 210. The logic engine 210 may represent hardware, software, firmware, or any combination thereof. In one embodiment, the logic engine 210 may include one or more processors. The logic engine 210 may also represent an application specific integrated circuit (ASIC) or field programmable gate array (FPGA). The logic engine 210 may utilize sensor measurements, user input, user preferences and settings, conditions, factors, and environmental conditions to determine the identity of the user, at least in part, from measurements performed by the wireless earpieces 202. The identity of the user may be utilized by the logic engine 210 to manage specific calibration of the sensors 217. For example, the logic engine 210 may detect conditions that may necessitate calibration, such as device initiation, a power reset, large temperature swing, substantial impact, pressure/altitude chance, or so forth.

In one embodiment, the logic engine 210 may manage the sensor calibrations based on measurements and data from the sensors 217 as well as other connected devices. The logic engine 210 may also perform any number of mathematical functions (e.g. linear extrapolation, polynomial extrapolation, conic extrapolation, French curve extrapolation, polynomial interpretation) to determine or infer the correct sensor configuration, biasing, or adjustments that may be required. The logic engine 210 may utilize historical measurements, trends, component degradation or failures, time, and other sensor measurements as causal forces to enhance a mathematical function utilized to perform the determinations, processing, and extrapolation performed by the logic engine 210.

The logic engine 210 may also process user input to determine calibration commands implemented by the wireless earpieces 202 or sent to the wireless earpieces 202 through the transceiver 216. Specific calibration commands or activities may be allowed based on sensor measurements, events, environmental conditions, proximity thresholds, and so forth. For example, the logic engine 210 may implement a calibration process macro allowing the user to run through various head positions and gestures to ensure that the wireless earpieces 202 are accurately detecting and interpreting measurements made by the sensors 217.

In one embodiment, a processor included in the logic engine 210 is circuitry or logic enabled to control execution of a set of instructions. The processor may be one or more microprocessors, digital signal processors, application-specific integrated circuits (ASIC), central processing units, or other devices suitable for controlling an electronic device including one or more hardware and software elements, executing software, instructions, programs, and applications, converting and processing signals and information, and performing other related tasks.

The memory 212 is a hardware element, device, or recording media configured to store data or instructions for subsequent retrieval or access at a later time. The memory 212 may represent static or dynamic memory. The memory 212 may include a hard disk, random access memory, cache, removable media drive, mass storage, or configuration suitable as storage for data, instructions, and information. In one embodiment, the memory 212 and the logic engine 210 may be integrated. The memory may use any type of volatile or non-volatile storage techniques and mediums. The memory 212 may store information related to the user, wireless earpieces 202, wireless device 204, and other peripherals, such as a wireless device, smart glasses, smart watch, smart case for the wireless earpieces 202, wearable device, and so forth. In one embodiment, the memory 212 may display or communicate instructions, programs, drivers, or an operating system for controlling the user interface 214 including one or more LEDs or other light emitting components, speakers, tactile generators (e.g. vibrator), and so forth. The memory 212 may also store biometric readings, user input required for specified calibration processes, calibration data (e.g., default, standard, baseline, factory programmed, preset, normative data—utilized for comparisons), user settings and preferences, thresholds, conditions, signal or processing activity, historical information, proximity data, and so forth.

The transceiver 216 is a component comprising both a transmitter and receiver which may be combined and share common circuitry on a single housing. The transceiver 216 may communicate utilizing NFMI, Bluetooth, Wi-Fi, ZigBee, Ant+, near field communications, wireless USB, infrared, mobile body area networks, ultra-wideband communications, cellular (e.g., 3G, 4G, 5G, PCS, GSM, etc.), infrared, or other suitable radio frequency standards, networks, protocols, or communications. For example, the transceiver 216 may coordinate communications and actions between the wireless earpieces 202 utilizing NFMI communications. The transceiver 216 may also be a hybrid transceiver that supports a number of different communications. For example, the transceiver 216 may communicate with wireless devices or other systems utilizing wired interfaces (e.g., wires, traces, etc.), NFC or Bluetooth communications. The transceiver 216 may also detect amplitudes and infer distance between the wireless earpieces 202 and external devices, such as the wireless device or a smart case of the wireless earpieces 202.

The components of the wireless earpieces 202 may be electrically connected utilizing any number of wires, contact points, leads, busses, wireless interfaces, or so forth. In addition, the wireless earpieces 202 may include any number of computing and communications components, devices or elements which may include busses, motherboards, circuits, chips, sensors, ports, interfaces, cards, converters, adapters, connections, transceivers, displays, antennas, and other similar components. The physical interface 215 is hardware interface of the wireless earpieces 202 for connecting and communicating with wireless devices or other electrical components, devices, or systems.

The physical interface 215 may include any number of pins, arms, or connectors for electrically interfacing with the contacts or other interface components of external devices or other charging or synchronization devices. For example, the physical interface 215 may be a micro USB port. In one embodiment, the physical interface 215 is a magnetic interface that automatically couples to contacts or an interface of a wireless device. In another embodiment, the physical interface 215 may include a wireless inductor for charging the wireless earpieces 202 without a physical connection to a charging device.

The user interface 214 is a hardware interface for receiving commands, instructions, or input through the touch (haptics) of the user, voice commands, or predefined motions. For example, the user interface 214 may include a touch screen (including a fingerprint scanner), one or more cameras or image sensors, microphones, speakers, and so forth. The user interface 214 may be utilized to control other functions of the wireless earpieces 202. The user interface 214 may include the LED array, one or more touch sensitive buttons or portions, a miniature screen or display, or other input/output components. The user interface 214 may be controlled by the user or based on commands received from the wireless device. For example, the user may turn on, reactivate, or provide feedback utilizing the user interface 214.

In one embodiment, the biometric data of the user may be encrypted and stored within a secure portion of the memory 212 to prevent unwanted access or hacking. The wireless earpieces 202 may also store important biometric data, such as medical information (e.g., medical conditions, allergies, logged biometrics, contacts, etc.) that may be shared in response to an emergency.

In one embodiment, the user may provide user feedback for implementing a calibration process by tapping the user interface 214 once, twice, three times, or any number of times. Similarly, a swiping or specific motion may be utilized across or in front of the user interface 214 (e.g., the exterior surface of the wireless earpieces 202) to implement a predefined action. Swiping motions in any number of directions or gestures may be associated with calibration or re-calibration as well as other activities, such as share exercise data, share music playlist, share vitals, play music, pause, fast forward, rewind, activate a digital assistant (e.g., Siri, Cortana, smart assistant, etc.), or so forth without limitation. The swiping motions may also be utilized to control actions and functionality of wireless devices or other external devices (e.g., smart television, camera array, smart watch, etc.). The user may also provide user input for authorizing or initiating a calibration process by moving his head in a particular direction or motion or based on the user's position or location. For example, the user may utilize voice commands, head gestures, or touch commands to perform calibration. The user may be changing between activities (e.g., running, biking, swimming, etc.) and may want the sensors 217 to be specifically configured for the activity. The user interface 214 may also provide a software interface including any number of icons, soft buttons, windows, links, graphical display elements, and so forth.

In one embodiment, the user interface 214 may periodically utilize one or more microphones and speakers of the wireless earpieces to authenticate the user. The microphone of the user interface 214 may measure various voice characteristics including amplitude, shimmer rates (i.e., changes in amplitude over time) frequency/pitch, jitter rates (i.e., changes in frequency data over time), accent, voice speed, inflection, and so forth. The wireless earpieces 202 may also recognize a pre-defined vocabulary, words, passwords, or phrases for authentication. For example, specific words may be required to authenticate the user and specific data associated with the user (e.g., fit of the wireless earpieces, baseline calibration readings, user preferences, etc.).

The sensors 217 may include pulse oximeters, accelerometers, gyroscopes, magnetometers, water, moisture, or humidity detectors, impact/flame detectors, thermometers, inertial sensors, photo detectors, miniature cameras, microphones, and other similar instruments for detecting the user's status as well as location, utilization of the wireless earpieces 202, orientation, motion, and so forth. The sensors 217 may also be utilized to determine the biometric, activity, location, and speed measurements of the user. In one embodiment, the sensors 217 may store data that may be shared with other components (e.g., logic engine 210 authenticating a calibration process), users, and devices.

The sensors 217 may also include photodetectors, ultrasonic mapping devices, or radar that scan the ear of the user when positioned for utilization. The sensors 217 may generate a two or three dimensional scan or topography map of the user's ear and surrounding areas when the wireless earpieces 202 are properly positioned. The mapping may include the internal and/or external portions of the user's ear. The topographical image of the user's ear may be utilized as a stand-alone biometric identifier or may be utilized with other biometric identifiers to identify the user. The topographical image may also be utilized to perform calibration based on the determined position, orientation, and fit of the sensors 217. The image may include the external auditory meatus, scapha, fossa triangularis, scaphoid fossa, antihelix antitragus, lobule, the tragus, and pinna as well as other internal or external portions of the ear and surrounding head structure.

The sensors 217 may pass measurements to the logic engine 210 for performing calibration processes and algorithms. Likewise, the memory 212 may store the calibration programs, algorithms, steps, baseline data, sensor measurement data, and so forth. This data and information may also be communicated to a connected device for storage or analysis. The sensor measurements may be compared against the baseline data to determine variations and how to compensate or adjust the wireless earpieces 202 based on the sensor measurements. The sensors 217 may also measure a noise floor of the sensors for each sensor of the wireless earpieces 202. The noise floor may be the measure of the signal created from the sum of all the noise sources and unwanted signals for each of the sensors 217 within each of the wireless earpieces 202. The noise floor may be calculated for various environments, locations, and positions all of which may affect the sensors 217. The logic engine 210 may also perform pattern analysis with the sensor measurements to calibrate or tune the sensors 217 based on established patterns or information.

Externally connected wireless devices may include components similar in structure and functionality to those shown for the wireless earpieces 202. For example, a wireless device may include any number of processors, batteries, memories, busses, motherboards, chips, transceivers, peripherals, sensors, displays, cards, ports, adapters, interconnects, sensors, and so forth. In one embodiment, the wireless device may include one or more processors and memories for storing instructions. The instructions may be executed as part of an operating system, application, browser, or so forth to implement the features herein described. For example, the user may set preferences for the wireless earpieces 202 to perform calibration based on specified events, locations, activities, or user input. Likewise, the preferences may manage the actions taken by the wireless earpieces 202 in response to identifying specific users are utilizing the wireless earpieces 202. For example, a parent user may require a comprehensive calibration process for the size and shape of her ear and a juvenile user may have a second more limited calibration process performed when utilizing the wireless earpieces 202 or vice versa. In one embodiment, the wireless earpieces 202 may be magnetically or physically coupled to the wireless device to be recharged or synchronized.

The wireless device may also execute an application with settings or conditions for updating, synchronizing, sharing, saving, identifying, calibrating, and utilizing biometric information as herein described. For example, one of the sensors 217 that may have failed may be ignored in response to improper or unreliable data being gathered. As a result, the user identification process for calibration process authorization may be dynamically performed utilizing any combination of sensor measurements. For example, the number and position of the sensors 217 utilized to perform sensor measurements of the user may vary based on failures, inaccurate data, or other temporary or permanent issues with hardware and software of the wireless earpieces 202.

Figure 3:
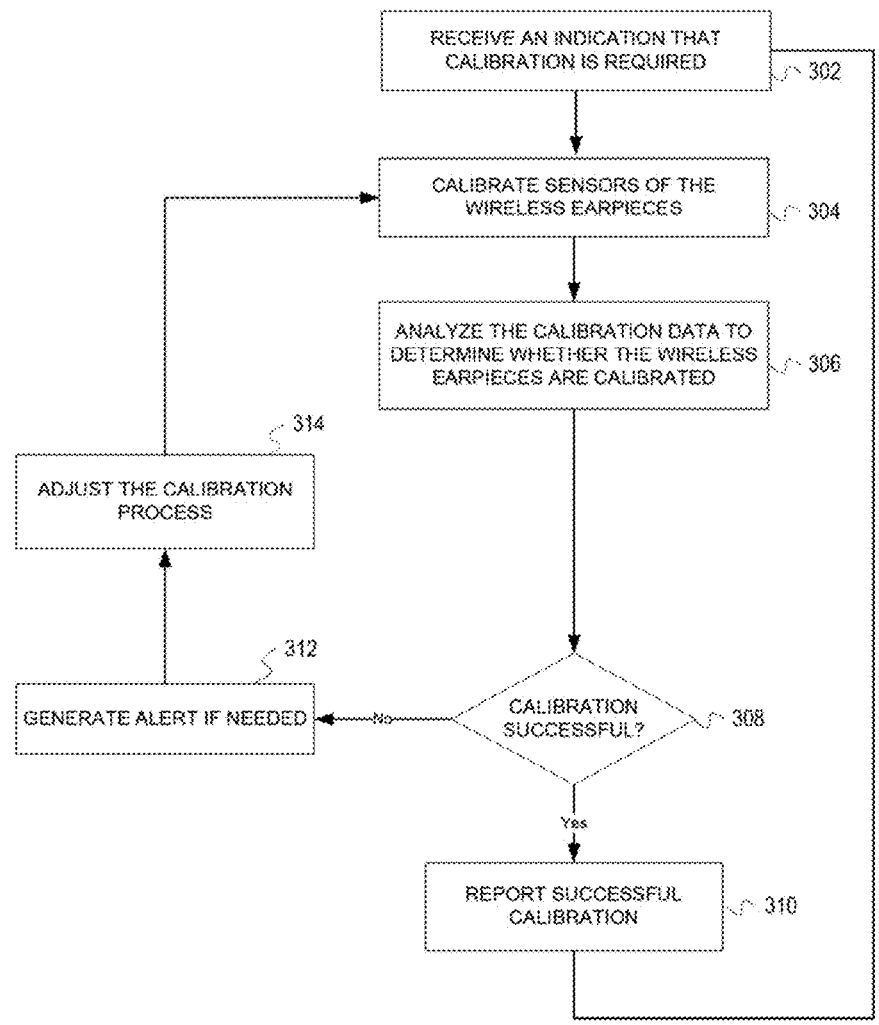
FIG. 3 is a flowchart of a process for calibrating the wireless earpieces in accordance with an illustrative embodiment.

FIG. 3 is a flowchart of a process for calibrating the wireless earpieces in accordance with an illustrative embodiment. In one embodiment, the process of FIG. 3 may be implemented by one or more wireless earpieces, such as the wireless earpieces 102 of FIG. 1. For example, the method of FIG. 3 may be performed for both of the wireless earpieces as a pair/set or for each of wireless earpieces individually to calibrate individual sensors or the sensor arrays of the wireless earpieces.

In one embodiment, the biometric readings and user input may include one or more of pulse rate, hand gestures, designated motions, voice amplitude, ear/head topography, voice frequency, skin conductivity, vocabulary, blood oxygenation, temperature, calories expended per time period, sweat levels, orientation, position, and so forth. The method of FIG. 3 may be performed to implement a calibration process. For example, the existing sensors of the wireless earpieces may be calibrated, re-calibrated, or otherwise configured for individual users, environments, activities, or conditions. The process of FIG. 3 may be performed by one or more of the wireless earpieces and a wireless device (e.g., cell phone, tablet, gaming device, smart card, etc.). Each step of the process of FIG. 3 may include an alert or other indicator that indicates the status of the calibration to the user. The alerts may be communicated audibly, textually, tactilely or through any number of other communications processes available to the wireless earpieces or electronic device, its communication with the wireless earpieces.

The process may begin with the wireless earpieces receiving an indication that a calibration process is pending (step 302). The indication may be received by the wireless earpieces or may be self-determined. In one embodiment, the wireless earpieces may automatically perform a calibration process in response to set-up of the wireless earpieces, power up, a designated change in activities, a detected event (e.g., change in temperature beyond a threshold, sensed impact, altitude change, etc.). The calibration process may be initiated in response to one or more user or environmental threshold being reached. In one embodiment, the indication may be received directly from a user of the wireless earpieces. For example, the user may give a verbal command, such as "re-calibrate sensors." The ser may also be a pre-programmed voice command, gesture, head motion, or other input that may be sensed by the wireless earpieces. As a result, the calibration process may be initiated and processed entirely utilizing the wireless earpieces. In another embodiment, the indication may be received from a wireless device, such as a cell phone in communication with the wireless earpieces.

In some embodiments, the calibration process may be or include a diagnostic activity performed for all or portions of the sensors. The diagnostic may test functionality, accuracy, and any number of other factors. The process of step 302 may also involve identifying the user. The user may be identified to retrieve applicable information, data, and algorithms that may be utilized.

The indication may provide information that the wireless device requires for calibration. For example, the indication may be played as an audio or tactile alert to the wireless earpieces specifying that all or a portion of the sensors are being calibrated. Based on the conditions, calibration may be required for all of the sensor arrays of the wireless earpieces or for specified sensors. For example, in response to an extreme temperature swing being detected, all of the temperature sensors may be calibrated, in response to a sensed impact, the gyroscopes and accelerometers may be recalibrated, in response to a detected cardiovascular event, the pulse rate detector may be calibrated. In one embodiment, one or more applications or other software interfaces of both the wireless device and the wireless earpieces may interact to perform the process and steps of FIG. 3.

Next, the wireless earpieces calibrate sensors of the wireless earpieces (step 304). The calibration may include any number of mathematical, functional, software, or hardware tests, diagnostics, resets, biasing, and adjustments. The calibration may be performed for all, or a portion, of the sensors of the wireless earpieces. For example, only specific types of sensors (e.g., optical/imaging, thermal, touch sensors, audio, contact, etc.) may be tested. In one embodiment, the indication received in step 302 may specify the sensors calibrated during step 304. The calibration process may be specific to the user utilizing the wireless earpieces or may be generically performed to ensure proper operation and fit of the wireless earpieces within the ears of the user. In one embodiment, sensor measurements may be performed during step 304 for comparison against baseline, default, ideal, or standard sensor measurements.

Next, the wireless earpieces analyze the calibration data to determine whether the wireless earpieces are calibrated (step 306). The calibration data for the sensors may be taken in real-time and compared against baseline data for each of the wireless earpieces. The baseline data may be associated with one of a number of users that may utilize the wireless earpieces. In one embodiment, the calibration data may indicated whether the sensors are functional, non-functional, experiencing errors, problems, or other issues, or other conditions or settings associated with each of the sensors. The sensor readings may be analyzed for accuracy, statistical significance, and so forth. For example, the biometric readings may be compared against default, baseline, or standard biometric readings for the user to ensure accuracy in identifying the user. The wireless earpieces may also perform biasing, reconfiguration, or error correction as needed during step 304 to ensure the sensor measurements are accurate. For example, if a sensor from one of the wireless earpieces is experience incorrect or inaccurate data, the data from that sensor may be disregarded for purposes of performing analysis. The sensor measurements may be run through any number of computations utilizing the processor of the wireless earpiece. During step 306, any number of tests, diagnostics, or other processes may be implemented to facilitate calibration or as part of the calibration process itself.

Next, the wireless earpieces determine whether the calibration is successful (step 308). Calibration may be determined to be successful in response data received from the sensors or measurements taken by the sensors after the calibration has been implemented. For example, the sensor measurement data from a sensor of the left wireless earpiece may be compared against measurements made by secondary sensors of the left wireless earpieces, analogous sensors of the right wireless earpieces, or sensors of externally connected devices (e.g., cell phone, tablet, etc.). The calibration may also be determined to be successful in response to the wireless earpieces running one or more tests or diagnostics on the calibrated sensors.

If the calibration is determined to be successful in step 308, the wireless earpieces report successful calibration (step 310). In one embodiment, the report may include logging information in the memory of the wireless earpieces or a connected device. In another embodiment, an alert may be communicated to the user. For example, a beep, vibration, click, or audio message may indicate that one or more of the wireless earpieces have been successfully calibrated. The report may also be an alert that is sent to a wireless device in communication with the wireless earpieces. During step 310, the wireless earpieces may enter normal operation and functionality.

If the wireless earpieces determine that calibration is not successful during step 308, the wireless earpieces generate an alert if needed (step 312). The alert may be generated in any number of ways. In one embodiment, the alert is an internal alert that may be communicated to the user of the wireless device. For example, the alert may be communicated to the user as an audio, tactile, or visual alert, such as "the calibration process failed, try resetting the earpiece." The alert may also provide feedback for the user to troubleshoot the wireless earpieces. For example, the user may be encouraged to connect the wireless earpieces to a smart case, computer, or wireless device for more thorough troubleshooting. The alert may also be communicated to a wireless device in communication with the wireless earpiece. For example, an alert may be sent to a cell phone in communication with the wireless earpiece to display an application specific alert to the user, such as "the thermal sensors cannot be calibrated and may provide inaccurate data and information." In some embodiments, the alert may be sent through email, text message, or other designated communications technique in the event that the wireless earpieces are being utilized by an unauthorized party. In other embodiments, no alert may be generated.

Next, the wireless earpieces adjust the calibration process (step 314). In one embodiment, the bias levels or adjustments utilized may be reevaluated and changed. In another embodiment, the sensors may be completely shut down and restarted. The identify of the user may also be verified and authorized. The resection may be a default response to determining the user is not authorized to perform the calibration process. Next, the process returns again to step 304.

The process of FIG. 3 may allow the wireless earpieces to calibrate internal sensors. The process may be performed any number of times during start up, shut down, and normal operations of the wireless earpieces.

The illustrative embodiments provide a system, method, and wireless earpiece(s) for performing self-calibration automatically or based on detected events, activities, thresholds or user input. The illustrative embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments of the inventive subject matter may take the form of a computer program product embodied in any tangible medium of expression having computer usable program code embodied in the medium. The described embodiments may be provided as a computer program product, or software, that may include a machine-readable medium having stored thereon instructions, which may be used to program a computing system (or other electronic device(s)) to perform a process according to embodiments, whether presently described or not, since every conceivable variation is not enumerated herein. A machine readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions. In addition, embodiments may be embodied in an electrical, optical, acoustical or other form of propagated signal (e.g., carrier waves, infrared signals, digital signals, etc.), or wireline, wireless, or other communications medium.

Computer program code for carrying out operations of the embodiments may be written in any combination of one or more programming languages, including an object oriented programming language such as Java, Smalltalk, C++ or the like and conventional procedural programming languages such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a personal area network (PAN), or a wide area network (WAN), or the connection may be made to an external computer (e.g., through the Internet using an Internet Service Provider).

Figure 4:
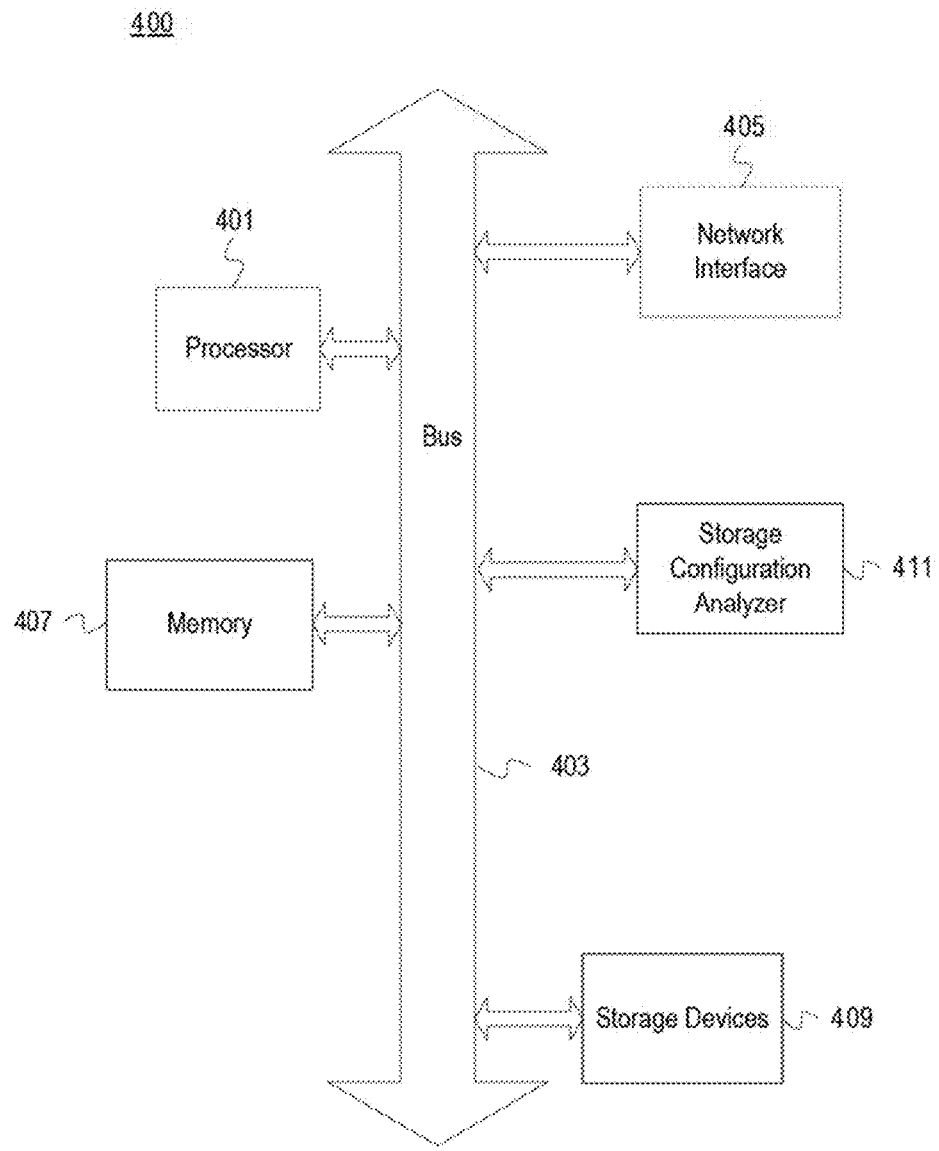
FIG. 4 depicts a computing system in accordance with an illustrative embodiment.

FIG. 4 depicts a computing system 400 in accordance with an illustrative embodiment. For example, the computing system 400 may represent an electronic computing or communications device, such as the wireless device 104 of FIG. 1. The computing device 400 may be utilized to receive user settings, instructions, or feedback for controlling the power management features of the wireless earpieces together and separately. The computing system 400 includes a processor unit 401 (possibly including multiple processors, multiple cores, multiple nodes, and/or implementing multi-threading, etc.). The computing system includes memory 407. The memory 407 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computing system also includes a bus 403 (e.g., PCI, ISA, PCI-Express, HyperTransport®, InfiniBand®, NuBus, etc.), a network interface 405 (e.g., an ATM interface, an Ethernet interface, a Frame Relay interface, SONET interface, wireless interface, etc.), and a storage device(s) 409 (e.g., optical storage, magnetic storage, etc.). The system memory 407 embodies functionality to implement embodiments described above. The system memory 407 may include one or more functionalities that facilitate retrieval of the audio information associated with an identifier. Code may be implemented in any of the other devices of the computing system 400. Any one of these functionalities may be partially (or entirely) implemented in hardware and/or on the processing unit 401. For example, the functionality may be implemented with an application specific integrated circuit, in logic implemented in the processing unit 401, in a co-processor on a peripheral device or card, etc. Further, realizations may include fewer or additional components not illustrated in FIG. 4 (e.g., video cards, audio cards, additional network interfaces, peripheral devices, etc.). The processor unit 401, the storage device(s) 409, and the network interface 405 are coupled to the bus 403. Although illustrated as being coupled to the bus 403, the memory 407 may be coupled to the processor unit 401.

The illustrative embodiments are not to be limited to the particular embodiments described herein. In particular, the illustrative embodiments contemplate numerous variations in the type of ways in which embodiments may be applied. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes or methods of the invention. It is understood that any other modifications, substitutions, and/or additions may be made, which are within the intended spirit and scope of the disclosure. For the foregoing, it can be seen that the disclosure accomplishes at least all of the intended objectives.

The previous detailed description is of a small number of embodiments for implementing the invention and is not intended to be limiting in scope. The following claims set forth a number of the embodiments of the invention disclosed with greater particularity.

What is claimed is:

1. A method for calibrating one or more wireless earpieces while worn by a user, the method comprising steps of:
   receiving an indication that calibration of the one or more wireless earpieces is required while the user is wearing the one or more wireless earpieces;
   directing a user of the one or more wireless earpieces to perform motions for use in calibration, wherein the directing is performed by the one or more wireless earpieces;
   acquiring inertial data at the one or more wireless earpieces during the motions from one or more accelerometers and one or more gyrometers;
   calibrating sensors of the one or more wireless earpieces in response to receiving the indication, wherein the sensors include the one or more accelerometers and the one or more gyrometers;
   analyzing calibration data collected during the step of calibrating the sensors of the one or more wireless earpieces; and
   determining whether the calibration is successful utilizing the calibration data to set a threshold.

2. The method of claim 1, wherein the indication is received from a wireless device associated with the one or more wireless earpieces.

3. The method of claim 1, further comprising:
   identifying a user wearing the one or more wireless earpieces utilizing one or more biometric identifiers.

4. The method of claim 3, wherein the calibrating is performed utilizing information associated with the user.

5. The method of claim 1, wherein the biometric identifiers include one or more of voice characteristics, ear topography, and skin conductivity.

6. The method of claim 1, wherein the one or more wireless earpieces are a pair of wireless earpieces.

7. The method of claim 1, wherein the indication is self-determined by the one or more wireless earpieces in response to one or more of a setup process being initiated, and power up process being initiated, one or more thresholds being met, and a detected event.

8. The method of claim 1, wherein the sensors are a sensor array of the one or more wireless earpieces.

9. The method of claim 1, wherein the calibrating is performed utilizing baseline data associated with a user wearing the one or more wireless earpieces.

10. The method of claim 9, wherein the calibrating further comprises:
    detecting one or more aberrations of sensor measurements as compared against baseline measurements of a user wearing the one or more wireless earpieces.

* * * * *